(12) United States Patent
Ohara et al.

(10) Patent No.: US 6,514,210 B2
(45) Date of Patent: Feb. 4, 2003

(54) FORWARD VIEWING AND RADIAL SCANNING ULTRASONIC ENDOSCOPE

(75) Inventors: Kenichi Ohara, Gunma (JP); Toshiyuki Hashiyama, Saitama (JP)

(73) Assignee: Pentax Corporation, Tokyo (JP)

( * ) Notice: Subject to any disclaimer, the term of this patent is extended or adjusted under 35 U.S.C. 154(b) by 0 days.

(21) Appl. No.: 09/850,225

(22) Filed: May 8, 2001

(65) Prior Publication Data

US 2001/0041839 A1 Nov. 15, 2001

(30) Foreign Application Priority Data

May 10, 2000 (JP) ........................................ 2000-136733

(51) Int. Cl.⁷ ................................................ A61B 8/12
(52) U.S. Cl. ........................................ 600/462; 600/463
(58) Field of Search ................................. 600/462, 459, 600/463, 439, 160, 423, 445, 116, 431, 156, 440; 348/75

(56) References Cited

U.S. PATENT DOCUMENTS 4,998,182 A  *  3/1991  Krauter et al. ................. 348/75
5,873,828 A  *  2/1999  Fujio et al. .................... 600/439
6,095,970 A     8/2000  Hidaka et al.
6,193,666 B1 *  2/2001  Ouchi ........................... 600/459

FOREIGN PATENT DOCUMENTS

JP          2-265534          10/1990

* cited by examiner

*Primary Examiner*—Marvin M. Lateef
*Assistant Examiner*—Ruby Jain
(74) *Attorney, Agent, or Firm*—Greenblum & Bernstein, P.L.C.

(57) ABSTRACT

In a radial scan, forward viewing ultrasonic endoscope, centering mating portions that permit the outer surface of an ultrasonic probe and the outer surface of a tip body to meet flush with each other at the boundary are formed in the ultrasonic probe and in the tip body and the gap between the inner peripheral surface of the ultrasonic probe and the mating surface of the front half of the tip body is formed to be larger than the gap between the centering mating portions.

24 Claims, 11 Drawing Sheets

FIG. 12

FORWARD VIEWING AND RADIAL SCANNING ULTRASONIC ENDOSCOPE

BACKGROUND OF THE INVENTION

The present invention relates to a radial scan, forward viewing ultrasonic endoscope having, at the tip of an insertion portion, objective optics for optical examination of the area ahead of said insertion portion and an ultrasonic probe for performing radial scan by ultrasound.

For ultrasonic endoscopes that can optically examine a body cavity while performing ultrasonic scan, it is generally considered advisable to project ultrasonic waves from the tip of an insertion portion to perform lateral scan on the area which lies the nearest to the scanning direction to be examined optically. The conventional ultrasonic endoscopes are structurally designed to meet this requirement.

However, the greatest value of ultrasonic endoscopes lies in inserting the ultrasonic endoscope into an accessible organ adjacent to the inaccessible organ which has problems and performing ultrasonic scan from the accessible organ by obtaining an ultrasonic cross-sectional image of the other side of an abnormal area of the mucous membrane in the body cavity of interst.

Therefore, effective ultrasonic scan is inmost cases radial scan about the longitudinal axis of the tip of the insertion portion whereas effective optical examination is forward viewing which is most convenient for checking the area ahead of the insertion portion of the endoscope as it passes through the body cavity.

However, ultrasonic endoscopes of this type that are commonly called "radial scan, forward viewing ultrasonic endoscopes" have several problems to solve, such as designing a structure that can shorten the rigid tip, and no commercial product has been put on the market.

SUMMARY OF THE INVENTION

An object, therefore, of the present invention is to provide a practically feasible radial scan, forward viewing ultrasonic endoscope that can minimize the length of the rigid tip of the insertion portion.

This object of the invention can be attained by a radial scan, forward viewing ultrasonic endoscope having an ultrasonic probe that is formed in annular shape to perform radial scan and which is provided at the tip of an insertion portion and a tip body that is fitted with objective optics for examining the area ahead of the insertion portion and that has a smaller outside diameter in the front half which is fitted into the ultrasonic probe, characterized in that centering mating portions that permit the outer surface of the ultrasonic probe and that of the tip body to meet flush with each other at the boundary are formed in the ultrasonic probe and in the tip body, and that the gap between the inner peripheral surface of the ultrasonic probe and the mating surface of the front half of the tip body is formed to be larger than the gap bet ween the centering mating portions.

In a preferred embodiment, the ultrasonic probe has an array of ultrasonic vibrators and an annular receptacle for holding the array of ultrasonic vibrators, the front half of the tip body is fitted into the internal space of the array of ultrasonic vibrators, and the centering mating portions are formed in the receptacle.

The present disclosure relates to the subject matter contained in Japanese patent application No. 2000-136733 (filed on May 10, 2000), which is expressly incorporated herein by reference in its entirety.

DESCRIPTION OF THE PREFERRED EMBODIMENT

An example of the present invention is described below with reference to the accompanying drawings.

Figure 2:
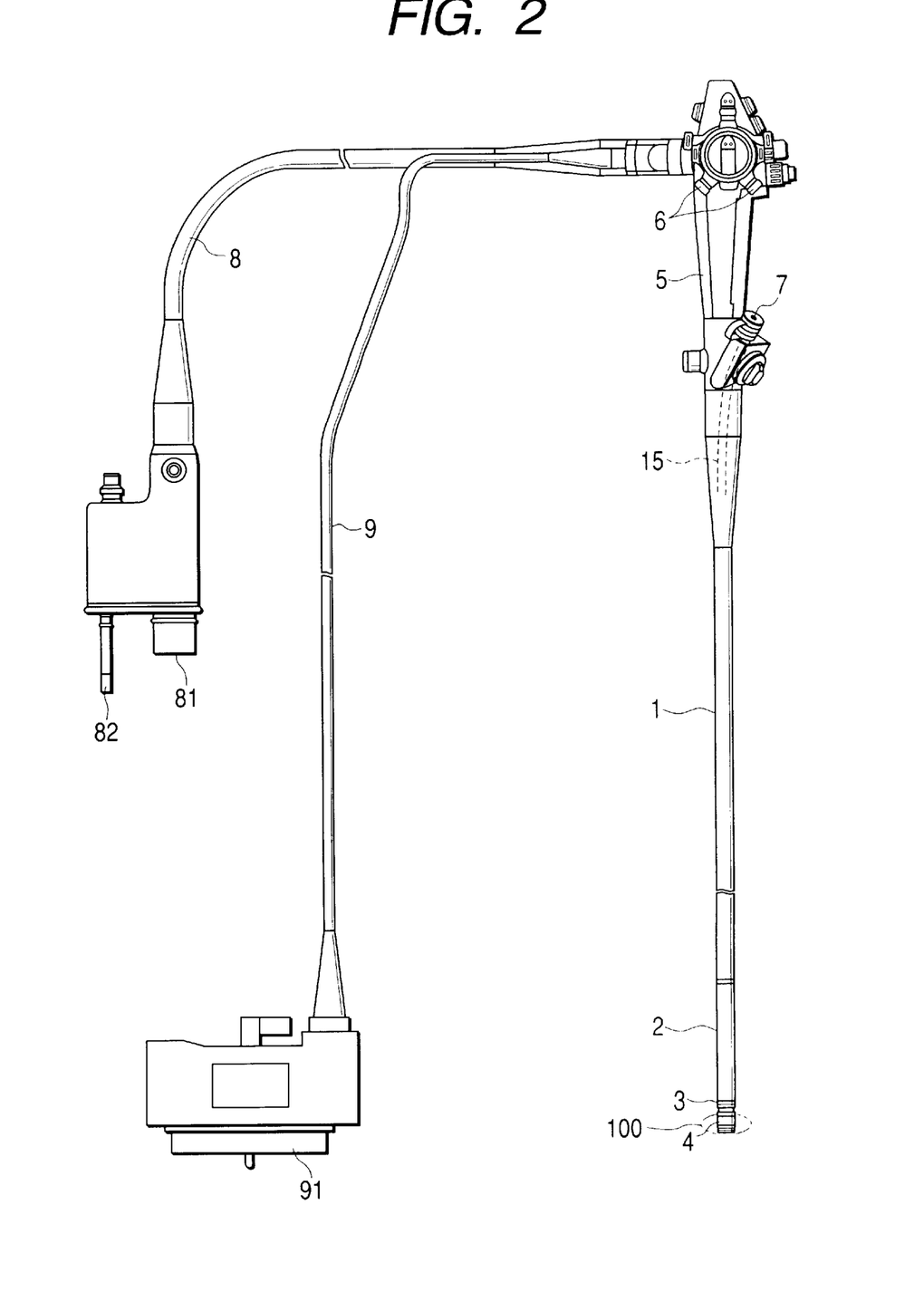
FIG. 2 is a side view showing the general layout of the radial scan, forward viewing ultrasonic endoscope.

FIG. 2 shows a radial scan, forward viewing ultrasonic endoscope. It comprises a flexible tube 1, a bending portion 2, a tip body 3 and an ultrasonic probe 4. The flexible tube 1 is to be inserted into a body cavity. The bending portion 2 is remotely manipulated to bend in various directions and coupled to the distal end of the flexible tube 1. The tip body 3 is coupled to the distal end of the bending portion 2. The ultrasonic probe 4 is fitted to the tip body 3. An inflatable balloon 100 is detachably provided around the ultrasonic probe 4.

A manipulating section 5 is coupled to the basal end of the flexible tube 1 and has knobs 6 for manipulating the bending portion 2 to bend in desired directions. Indicated by 7 is an opening through which a treatment tool or the like is inserted into a treatment tool insertion channel 15 extending through the flexible tube 1.

Two other flexible tubes 8 and 9 are coupled to the manipulating section 5. There are a video signal connector 81 which is connected to a video processor (not shown) and a lightguide connector 82 side by side at the distal end of the flexible tube 8. At the distal end of the flexible tube 9, there is an ultrasonic signal connector 91 which is connected to an ultrasonic signal processor (also not shown).

Figure 1:
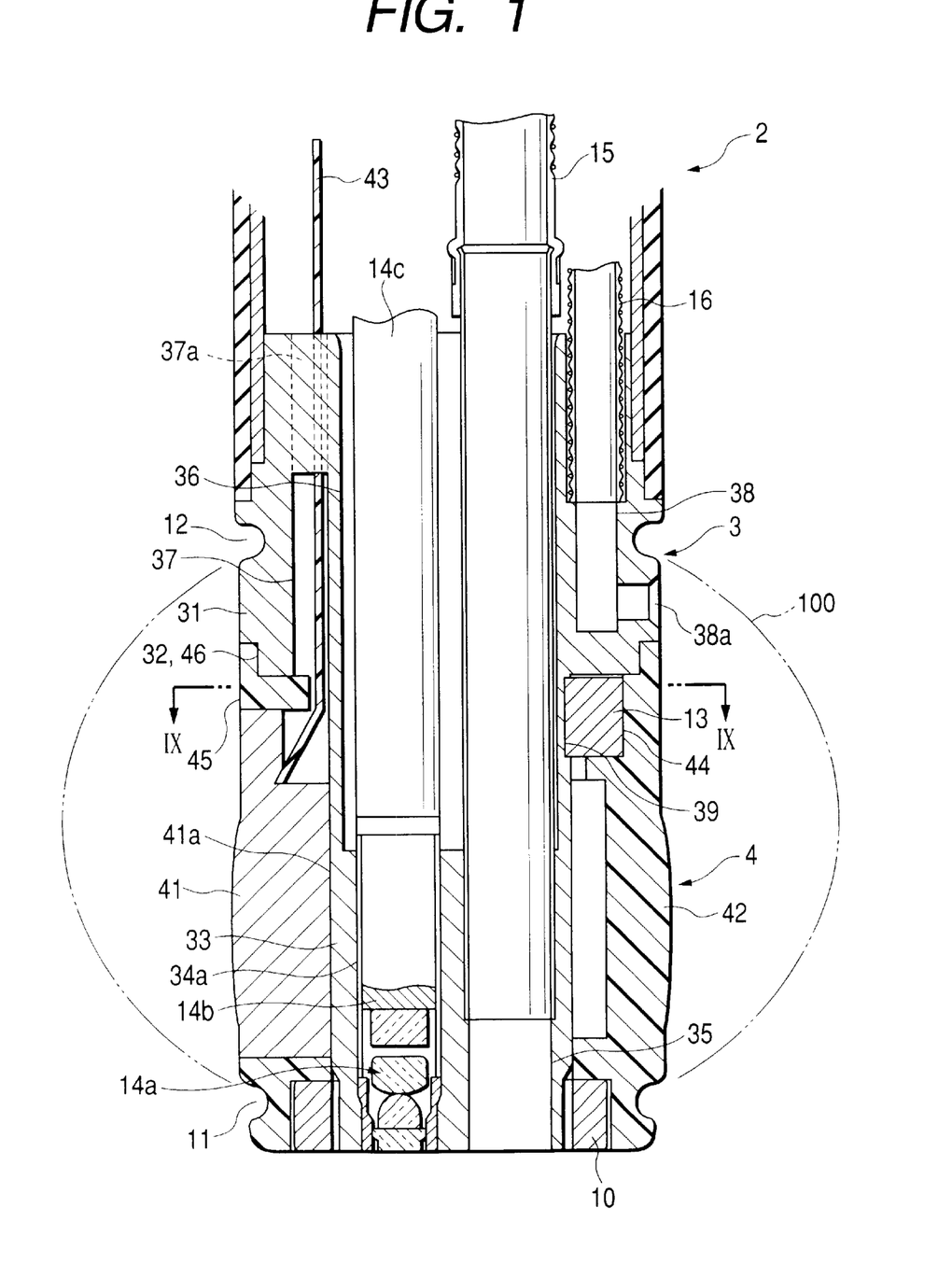
FIG. 1 is a longitudinal section of the tip of the insertion portion of a radial scan, forward viewing ultrasonic endoscope according to an example of the invention.

FIG. 1 shows the tip of the insertion portion. The ultrasonic probe 4 consists of a generally annular array of ultrasonic vibrators 41 that are held by a plastic receptacle 42 to form an united assembly (see FIG. 3).

Figure 3:
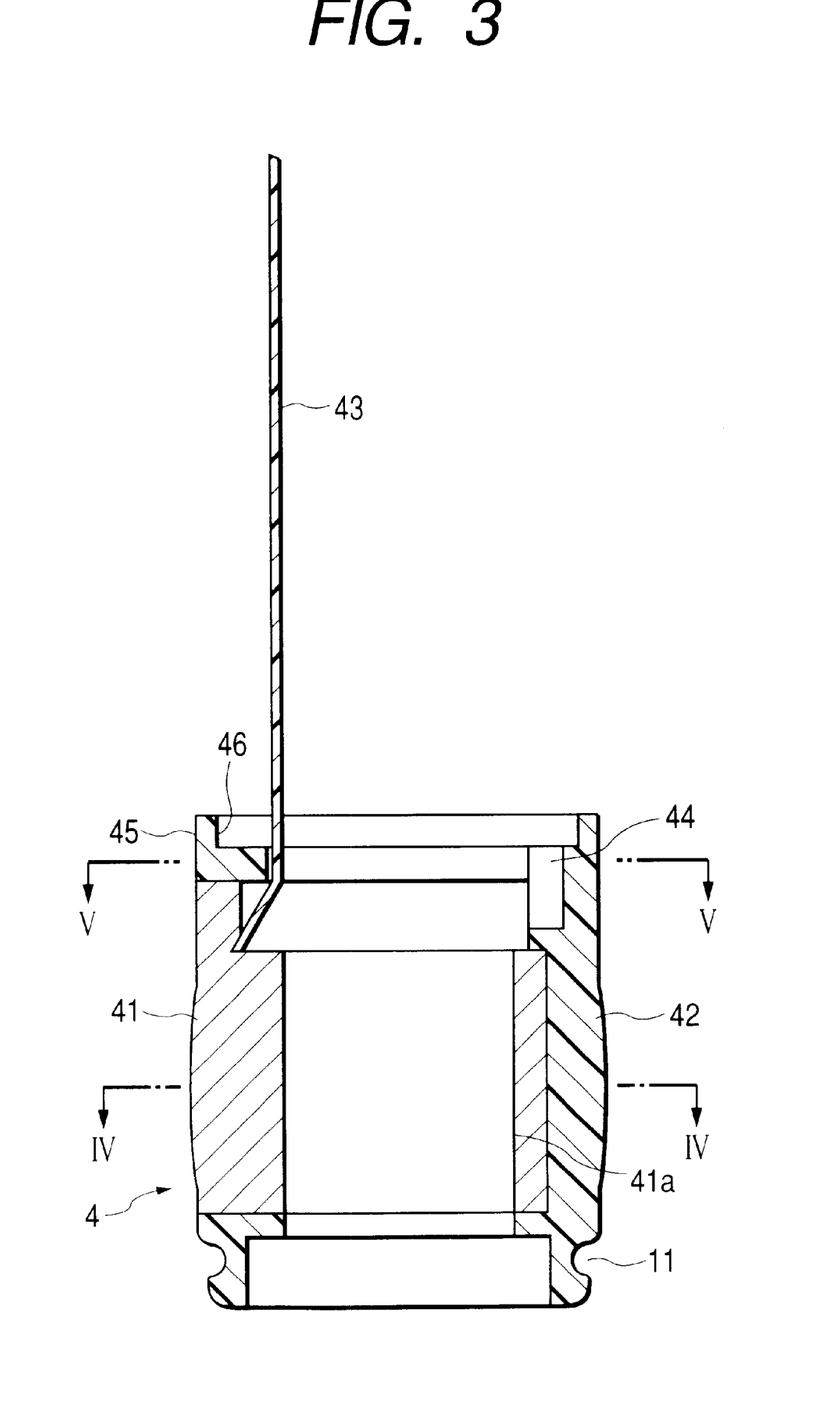
FIG. 3 is a longitudinal section of the ultrasonic probe in the example.
Figure 4:
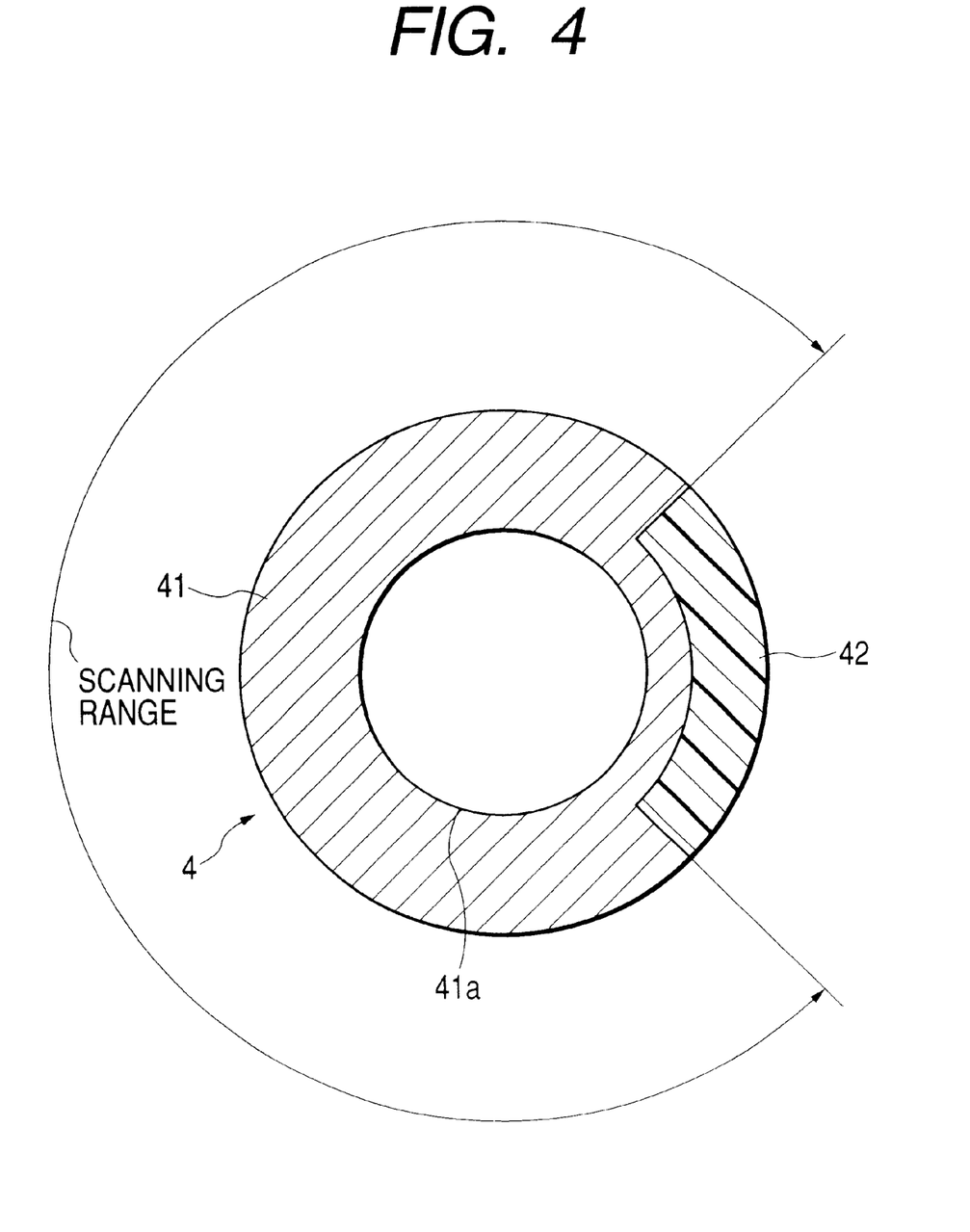
FIG. 4 is section IV—IV of FIG. 3.

As shown in FIG. 4 which is section IV—IV of FIG. 3, the array of ultrasonic vibrators 41 around the longitudinal axis of the insertion portion emit and receive ultrasonic signals successively (for electronic scan) through a certain angular range, say 270 degrees, around the longitudinal axis so as to perform radial scan in a direction perpendicular to the longitudinal axis.

The array of ultrasonic vibrators 41 has an internal space formed as a cylindrical hole centering on the longitudinal axis. Connected to the rear end of the array of ultrasonic vibrators 41 (upward in FIG. 3) are flexible boards 43 that are wired to transmit signals to and from the array of ultrasonic vibrators 41 and that extend rearward.

Figure 5:
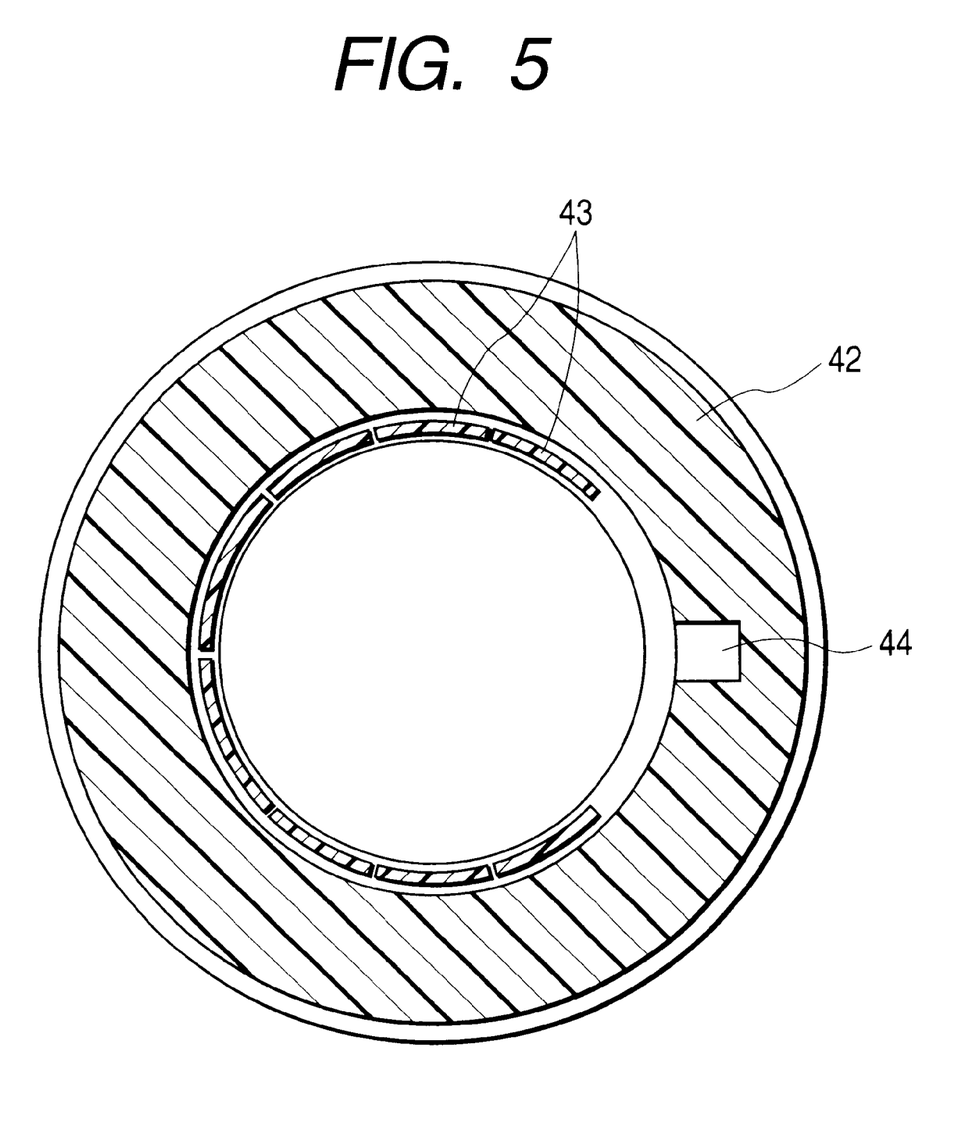
FIG. 5 is section IV—V of FIG. 3.

As shown in FIG. 5 which is section V—V of FIG. 3, the flexible boards 43 comprising eight pieces in the example shown are arranged in arcs about the longitudinal axis of the ultrasonic probe 4.

As is clear from FIG. 5, the flexible boards 43 are arranged in arcs through an angle of, say, about 270 degrees and that area of an extension of the series of arcs where no flexible board is provided has a groove 44 into which an anti-rotation member 13 to be described later is to be fitted.

Turning back to FIG. 3, the rear end portion of the receptacle 42 has a centering mating portion 46 that fits the centering mating portion 32 (to be described later) of the tip body 3 and which is formed in such a manner that it is concentric in high dimensional precision with the outer peripheral surface 45 (at the boundary where it meets the outer surface of the tip body 3). At the tip of the receptacle 42, a circumferential groove 11 is formed in the outer peripheral surface to assist in banding the distal end of the inflatable balloon 100.

Turning back again to FIG. 1, the tip body 3 typically made of plastics is so formed that the front half 33 has a size of small enough to fit the inner peripheral surface 41a of the array of ultrasonic vibrators 41 in the ultrasonic probe 4. The tip body 3 is shown as a single component in FIG. 6. The outer peripheral surface 31 of the tip body 3 at the boundary where it meets the outer peripheral surface of the ultrasonic probe 4 is of the same size as the outer peripheral surface 45 of the ultrasonic probe 4.

Figure 6:
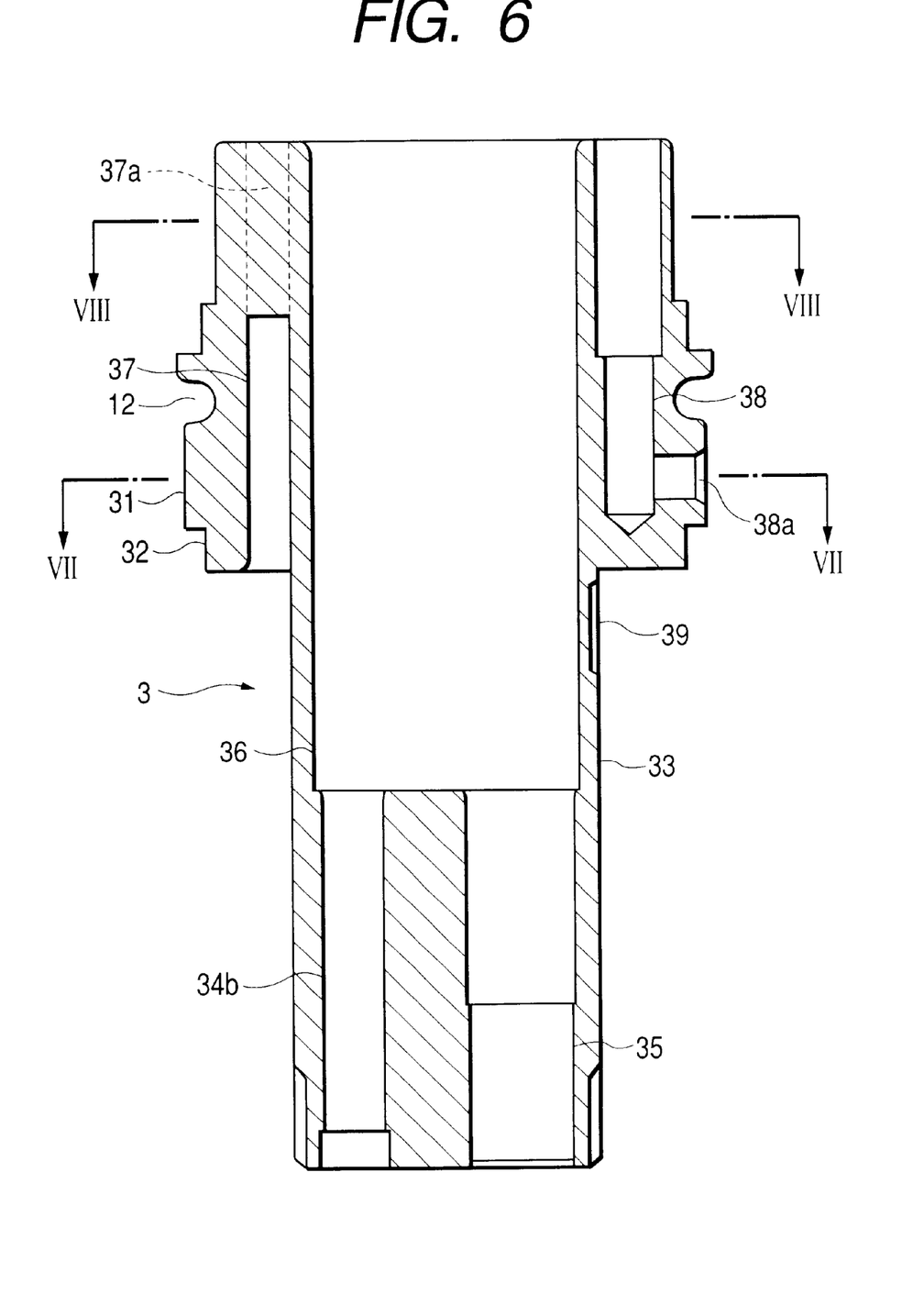
FIG. 6 is a longitudinal section of the tip body in the example.

The front end portion of the tip body 3 has, on the outer peripheral surface 31, the centering mating portion 32 that fits the centering mating portion 46 of the ultrasonic probe 4 and which is formed in such a manner that it is concentric in high dimensional precision with the outer peripheral surface 31. At the rear end of the tip body 3, a circumferential groove 12 is formed on the outer peripheral surface to assist in banding the rear end of the inflatable balloon 100.

The front half 33 of the tip body 3 has an objective optics accommodating hole 34a, an illumination light guide accommodating hole 34b and a treatment tool passage hole 35 formed parallel to the longitudinal axis in the area closer to the foremost end. Backward of this area is formed as a cable accommodating hole 36 whose inside diameter is slightly smaller than the outside diameter of the front half 33 and which extends to the rear end of the tip body 3.

Figure 7:
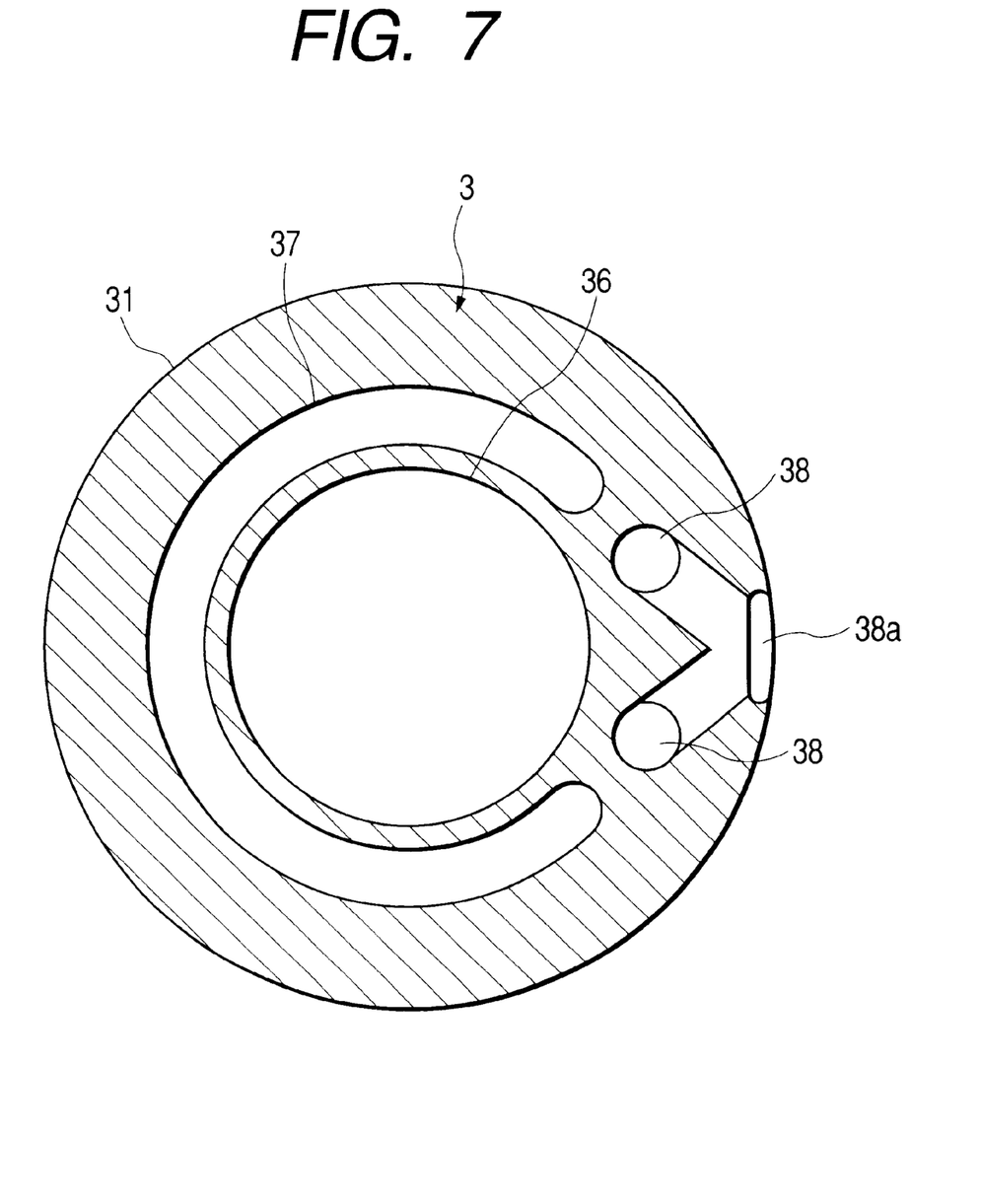
FIG. 7 is section VII—VII of FIG. 6.

The rear half of the tip body 3 has a flexible board passage hole 37 formed almost on an extension of the outer peripheral surface of the front half 33. The flexible board passage hole 37 admits the passage of flexible boards 43 and as shown enlarged in FIG. 7 which is section VII—VII of FIG. 6, it is formed in arc around the longitudinal axis with regard to the positions where the flexible boards 43 are arranged.

Figure 8:
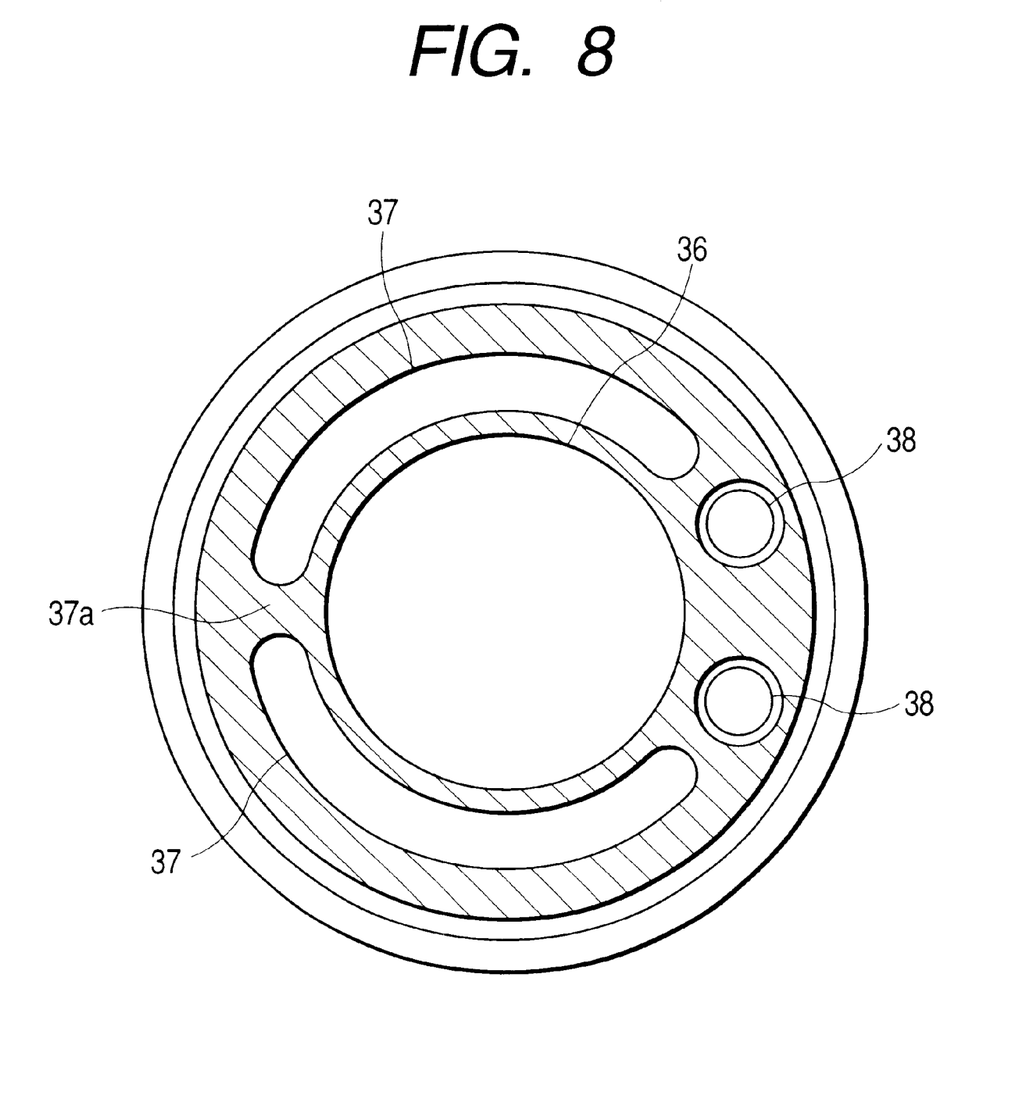
FIG. 8 is section VIII—VIII of FIG. 6.

Note that in the area of the tip body 3 which is near its rear end, at least one link 37a which interrupts the flexible board passage hole 37 part of the way is formed to secure the tip body 3 from being crushed under external force. This is shown enlarged in FIG. 8 which is section VIII—VIII of FIG. 6.

Turning back to FIGS. 6 and 7, the flexible board passage hole 37 is formed in arc through an angle of about 280 degrees. In the area which is an extension of the arc where no flexible board passage hole is formed, two fluid channels 38 through which deaerated water is injected into or drained from the balloon 100 are formed parallel to the longitudinal axis such that they communicate with an opening 38a into the balloon 100.

The two fluid channels 38 are formed side by side and one of them is for exclusive use in exhausting air. Actually, the fluid channels 38 do not appear in FIG. 6 (and FIG. 1) but for the sake of convenience in explanation, they are shown in those figures. Indicated by 39 is a groove into which the anti-rotation member 13 is to be fitted.

Turning back to FIG. 1, the ultrasonic probe 4 fitted over the front half 33 of the tip body 3 is urged and fixed against the surface of the intermediate step in the tip body 3 by means of a nut member 10 that meshes with the male thread formed on the outer periphery of the distal end of the tip body 3.

Figure 9:
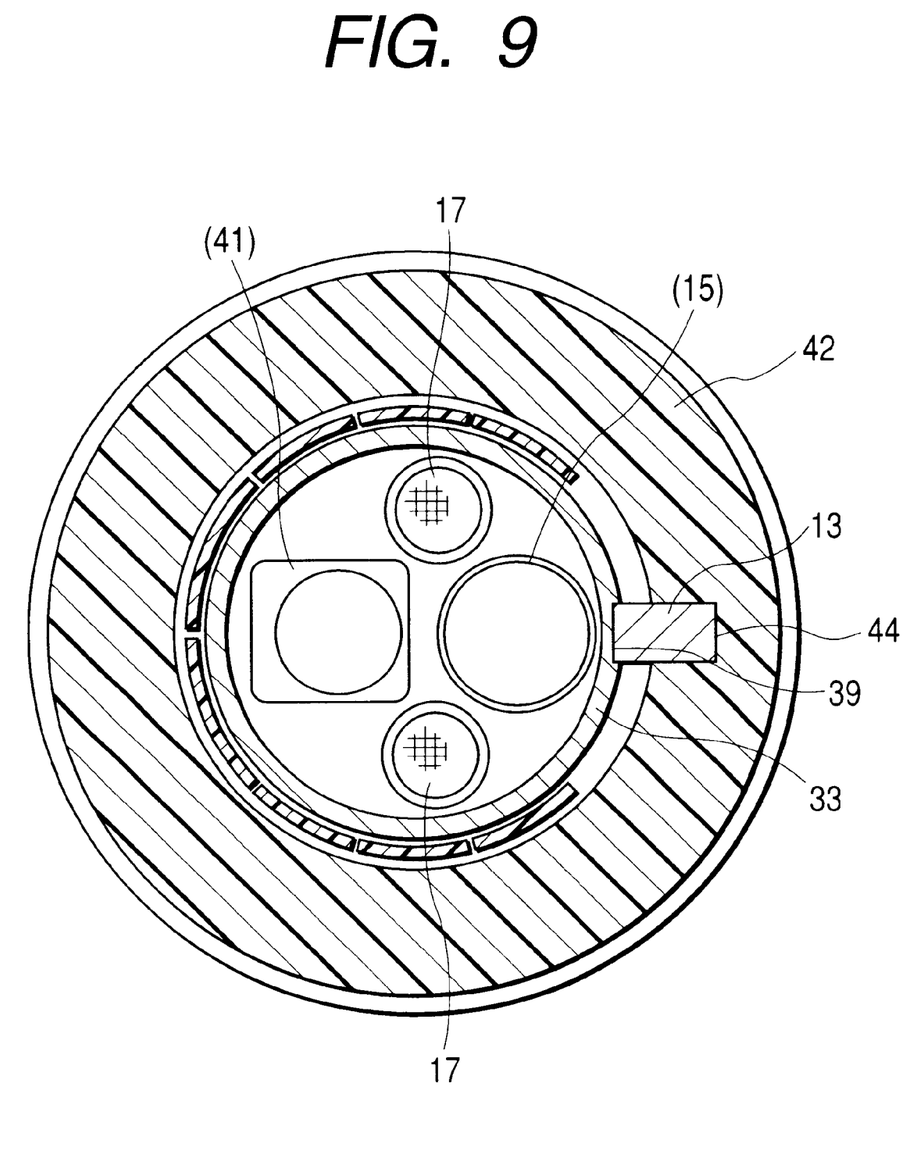
FIG. 9 is section IX—IX of FIG. 1.

As shown enlarged in FIG. 9 which is section IX—IX of FIG. 1, the anti-rotation member 13 in rectangular prism form is fitted into both the groove 44 in the ultrasonic probe 4 and the groove 39 in the tip body 3 so that the tip body 3 and the ultrasonic probe 4 to not rotate. This ensures that the direction of ultrasonic scan and the orientation of the viewing field for examination are set to satisfy the correct relationship. Indicated by 17 is a light guide fiber for illumination.

Turning back again to FIG. 1, when the ultrasonic probe 4 is fixed to the tip body 3, the front half 33 of the tip body 3 mates with the inner peripheral surface 41a of the array of ultrasonic vibrators 41 and the centering mating portion 32 of the tip body 3 mates with the centering mating portion 46 of the ultrasonic probe 4, because the gap in the former mating is formed to be larger than the gap between the mating portions in the latter case.

As a result, the seam between the tip body 3 and the ultrasonic probe 4 forms only a negligible difference in the exposed area where the outer peripheral surface 31 of the tip body 3 meets the outer peripheral surface 45 of the ultrasonic probe 4 and this contributes to forming an endoscope tip to be inserted smoothly into a body cavity of the patient.

Objective optics 14a are provided in the distal end portion of the objective optics accommodating hole 34 and a solid-state imaging device 14b is provided in the area behind them. A signal cable 14c for transmitting imaging signals and so forth passes through the cable passage hole 36 to extend rearward into the bending portion 2. The treatment tool insertion channel 15 is connected to the treatment tool passage hole 35 via a stainless steel pipe.

A flexible piping tube 16 is connected to each of the two fluid channels 38 and by operation of the manipulating section 5 and through these piping tubes 16, deaerated water is injected into and drained from the balloon 100 fixed at opposite ends by the peripheral grooves 11 and 12 so as to inflate and deflate the balloon 100.

As shown in FIG. 1, the flexible boards 43 which transmit signals to and from the array of ultrasonic vibrators 41 pass through the flexible board passage hole 37 in the tip body 3 to be guided rearward into the bending portion 2.

Figure 10:
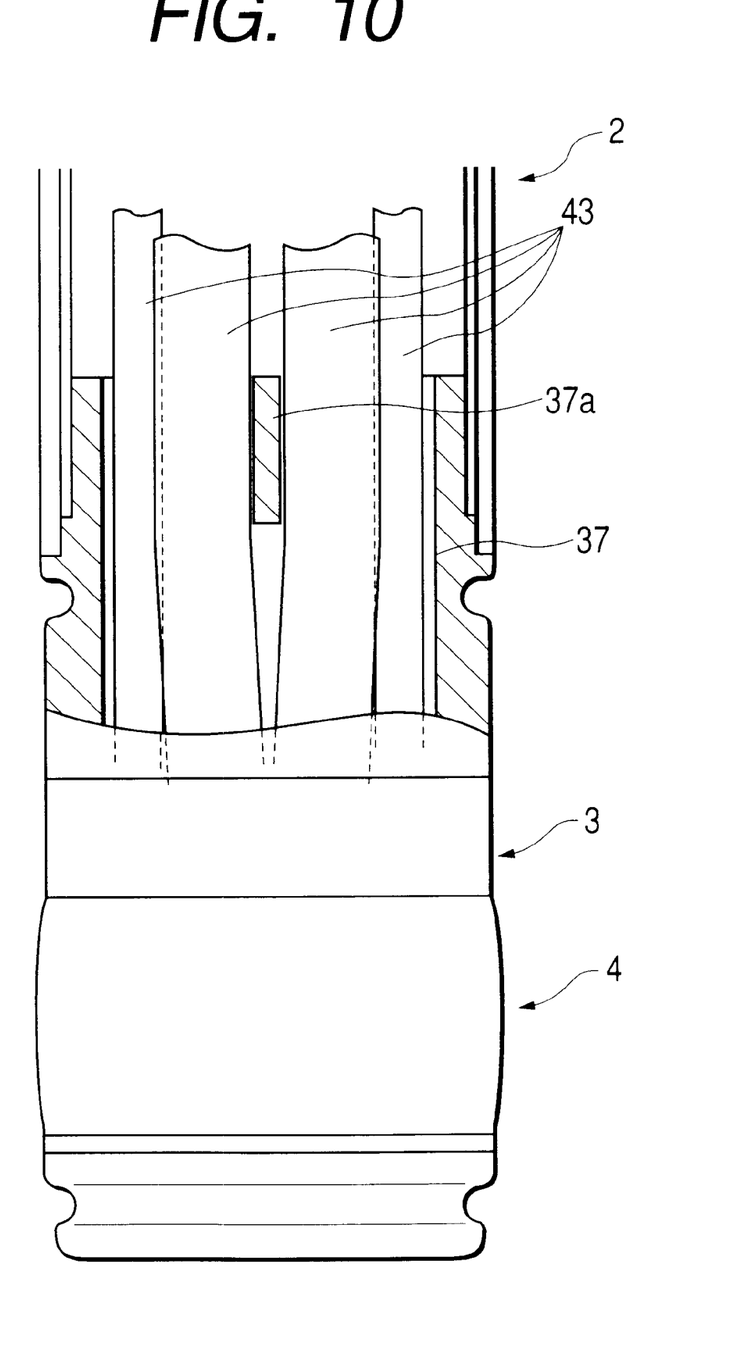
FIG. 10 is a partial sectional view showing how flexible boards pass through the bending portion in the example.

As is clear from FIG. 10, in the latter half of the flexible board passage hole 37, neighboring flexible boards 43 slightly overlap in order to avoid interference with the link 37a before they are guided rearward into the bending portion 2.

In the bending portion 2, all signals that are supplied into and output from the array of ultrasonic vibrators 41 are transmitted via the wiring formed on the thin flexible boards 43 so that there is no need to pass a signal cable and the like through the bending portion 2.

The flexible boards 43 are arranged in arcs that surround various inserts such as the signal cable 14c or the solid-state imaging device 14b, treatment tool insertion channel 15 and light-guide fiber 17. Hence, the various inserts are passed through the bending portion 2 in such a manner as to maximize the utilization of its internal space and this helps reduce its diameter.

Figure 11:
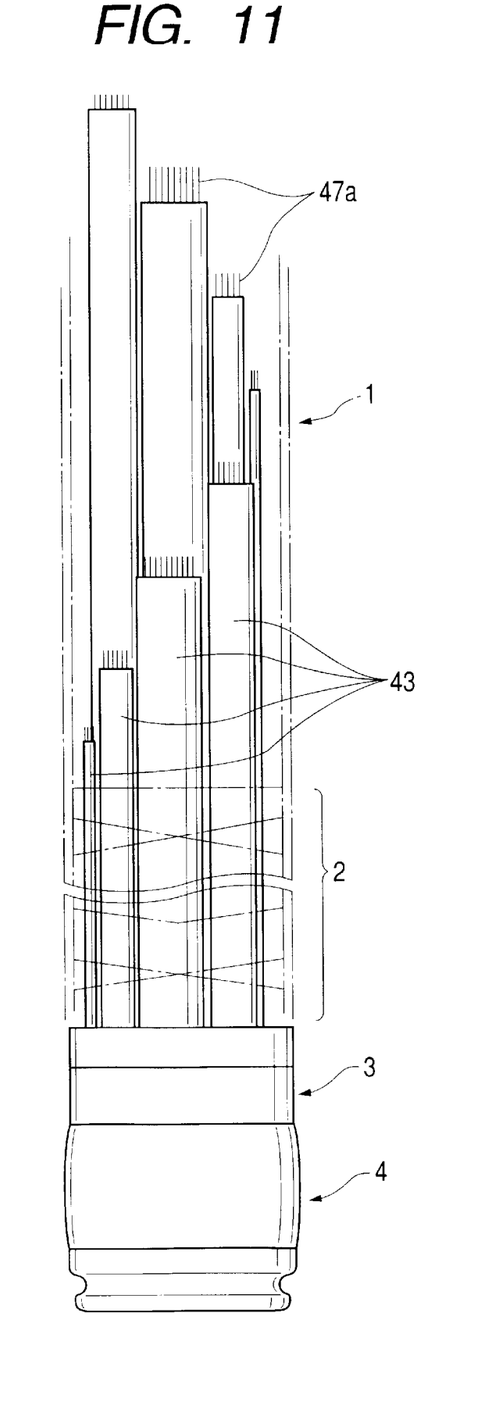
FIG. 11 is a sketch showing the ends of the flexible boards in the example.

As FIG. 11 shows, the flexible boards 43 vary in length but even the shortest one is long enough to pass through the bending portion 2 so that within the flexible tube 1 through which a signal cable 47 is passed, the individual flexible boards 43 are connected in longitudinally offset positions to the tips of the respective signal lines 47a in the cable 47.

The signal lines 47a in the cable 47 are soldered or otherwise connected to the flexible boards 43 and this can increase the diameter of each connection. However, in the present invention, the connections are longitudinally offset in position, so there is no possibility that their overall diameter unduly increases in certain areas and both the flexible tube 1 and the bending portion 2 can be formed in adequately small thickness.

Figure 12:
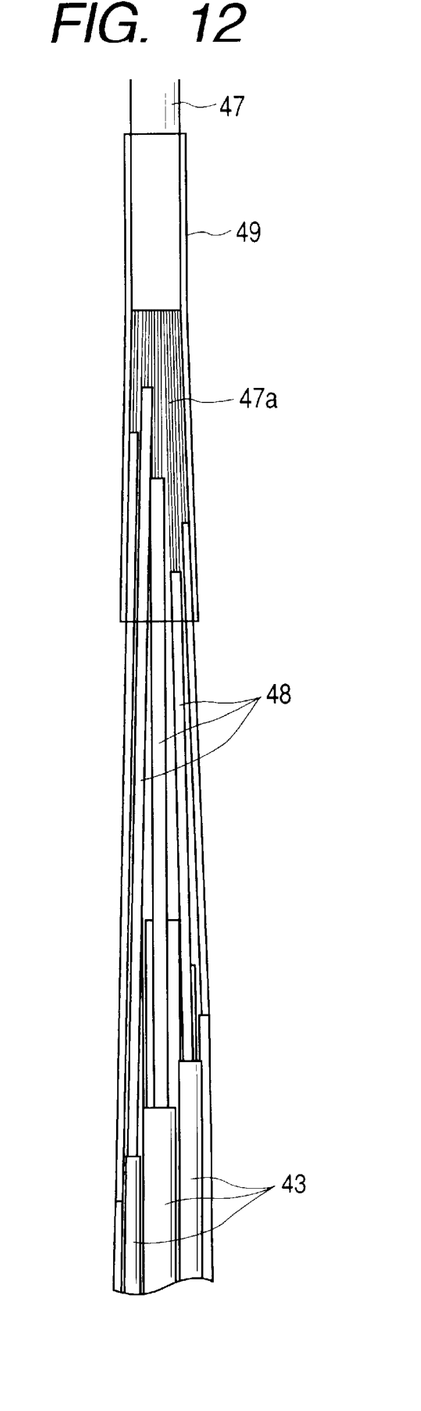
FIG. 12 is a side view of the area where the flexible boards are connected to the signal cable in the example.

FIG. 12 shows how the signal cable 47 is connected to the flexible boards 43 in the flexible tube 1. The distal end of the signal cable 47 which is a bundle of numerous signal lines 47a is disintegrated in the flexible tube 1 into individual signal lines 47a and a given number of signal lines 47a that are connected to each flexible board 43 are placed within a flexible heat-shrinking tube 48 which is subsequently shrunk to bind the encased signal lines together. This arrangement is effective to secure signal lines 47a from being broken.

The respective heat-shrinking tubes 48 are arranged in the offset position of their end. With this design, the flexibility of the flexible tube 1 will not change abruptly and the change in its overall diameter is so sufficiently smooth that there will be no possibility that the tube diameter increases in certain areas. All of the connections under consideration are bundled together within a thicker heat-shrunk flexible tube 49.

According to the invention, the gap between the inner peripheral surface of the ultrasonic tube and mating surface of the front half of the tip body is formed to be larger than the gap between the centering mating portions which enable the outer surfaces of the two members to be flush with each other at the boundary where they meet each other. As a result, the ultrasonic probe and the tip body can be coupled by a simple structural design without producing any differences and the rigid tip of the insertion portion is made as short as possible to fabricate an easily insertable and, hence, practically feasible radial scan, forward viewing ultrasonic endoscope.

What is claimed is:

1. A forward viewing and radial scanning ultrasonic endoscope comprising:
    an ultrasonic probe formed in an annular shape for performing radial scanning, said ultrasonic probe being provided at a tip of an insertion portion of said endoscope; and
    a tip body provided at the tip of said insertion portion of said endoscope, said tip body being fitted with objective optics for examining an area ahead of said insertion portion, a forward portion of said tip body having a smaller outside diameter than a rearward portion of said tip body, said forward portion of said tip body being configured so as to be fitted into said ultrasonic probe;
    wherein said ultrasonic probe and said tip body each include centering mating portions configured such that an outer surface of said ultrasonic probe and an outer surface of said rearward portion of said tip body meet flush with each other at a boundary therebetween along an outer surface of the tip of said insertion portion, and so that a gap between an inner peripheral surface of said ultrasonic probe and an outer surface of said forward portion of said tip body is larger than a gap between said centering mating portions of said ultrasonic probe and said tip body.

2. The forward viewing and radial scanning ultrasonic endoscope according to claim 1, wherein said ultrasonic probe includes an array of ultrasonic vibrators and an annular receptacle for holding the array of ultrasonic vibrators, said forward portion of said tip body being fitted into said array of ultrasonic vibrators and said centering mating portion of said ultrasonic probe being formed in said receptacle.

3. An ultrasonic endoscope comprising:
    a tip body having a larger diameter portion, a smaller diameter portion located adjacent to the larger diameter portion to define an intermediate step surface between the larger and smaller diameter portions, and a thread formed on an end of the smaller diameter portion opposite from the larger diameter portion;
    an ultrasonic probe, fitted on the smaller diameter portion, for performing radial scanning generally perpendicular to a longitudinal axis of said tip body; and
    a nut member threadingly engaged with the thread to fixedly hold said ultrasonic probe between the intermediate step surface and said nut member.

4. The ultrasonic endoscope according to claim 3, further comprising:
    a treatment tool insertion channel passed through an interior of the smaller diameter portion of said tip body and an interior of said ultrasonic probe to enable access of a treatment tool to a tissue in a body cavity in front of said nut member;
    an illumination system passed through the interior of the smaller diameter portion of said tip body and the interior of said ultrasonic probe to illuminate the tissue in the body cavity in front of said nut member; and
    an observing system passed through the interior of the smaller diameter portion of said tip body and the interior of said ultrasonic probe to observe the tissue in the body cavity in front of said nut member.

5. The ultrasonic endoscope according to claim 3, further comprising:
    an anti-rotation member, located adjacent to the intermediate step surface, for preventing relative rotation between an outer cylindrical surface of the smaller diameter portion and an inner cylindrical surface of said ultrasonic probe.

6. The ultrasonic endoscope according to claim 3, wherein said ultrasonic probe includes:
    a receptacle having a first annular end portion contacting the intermediate step surface, a second annular end portion defining a recess for accommodating said nut member therein, and a strut connecting the first annular end portion to the second annular end portion;
    a generally annular array of ultrasonic vibrators held by and between the first and second annular end portions in a longitudinal direction of said receptacle and by the strut in a circumferential direction of said receptacle; and
    a flexible board extending from said generally annular array and passing between an interior of the first annular end portion of said receptacle and the smaller diameter portion of said tip body.

7. The ultrasonic endoscope according to claim 3, further comprising:
an arcuate hole formed in said tip body within a predetermined angular range with respect to the longitudinal axis of said tip body, wherein a flexible board extending from the ultrasonic endoscope is passed through the arcuate hole; and
an opening for inflating and deflating a balloon, the opening being formed in said tip body outside the predetermined angular range.

8. The ultrasonic endoscope according to claim 7, further comprising:
a water drain and injection channel formed in said tip body outside the predetermined angular range; and
an air exhaust channel formed in said tip body outside the predetermined angular range;
wherein both of the channels communicate with the opening.

9. The ultrasonic endoscope according to claim 8, wherein the arcuate hole is divided into two arcuate hole sections by a reinforcement link of said tip body.

10. The ultrasonic endoscope according to claim 3, further comprising:
first and second grooves for cooperatively fixing an inflatable balloon onto the ultrasonic endoscope, said first and second grooves being respectively formed in said tip body and said ultrasonic probe.

11. An ultrasonic endoscope comprising:
a tip body;
an ultrasonic probe, fitted on said tip body, for performing radial scanning generally perpendicular to a longitudinal axis of said tip body;
a treatment tool insertion channel passed through an interior of said tip body and an interior of said ultrasonic probe to enable access of a treatment tool to a tissue in a body cavity in front of a distal end of said tip body beyond said ultrasonic probe;
an illumination system passed through the interior of said tip body and the interior of said ultrasonic probe to illuminate the tissue in the body cavity in front of the distal end of said tip body beyond said ultrasonic probe; and
an observing system passed through the interior of said tip body and the interior of said ultrasonic probe to observe the tissue in the body cavity in front of the distal end of said tip body beyond said ultrasonic probe.

12. The ultrasonic endoscope according to claim 11, wherein:
said tip body and said ultrasonic probe have a respective cylindrical outer surface and a cylindrical inner surface fitted together; and
an anti-rotation member is provided to prevent relative rotation between the cylindrical outer and inner surfaces when fitted together.

13. The ultrasonic endoscope according to claim 11, wherein said ultrasonic probe includes:
a receptacle having a first annular end portion, a second annular end portion, and a strut connecting the first annular end portion to the second annular end portion;
a generally annular array of ultrasonic vibrators held by and between the first and second annular end portions in a longitudinal direction of said receptacle and by the strut in a circumferential direction of said receptacle; and
a flexible board extending from said generally annular array and passed through an interior of the first annular end portion.

14. The ultrasonic endoscope according to claim 11, further comprising:
an arcuate hole formed in said tip body within a predetermined angular range with respect to the longitudinal axis of said tip body, wherein a flexible board extending from the ultrasonic endoscope is passed through the arcuate hole; and
an opening for inflating and deflating a balloon, the opening being formed in said tip body outside the predetermined angular range.

15. The ultrasonic endoscope according to claim 14, further comprising:
a water drain and injection channel formed in said tip body outside the predetermined angular range; and
an air exhaust channel formed in said tip body outside the predetermined angular range;
wherein both of the channels communicate with the opening.

16. The ultrasonic endoscope according to claim 15, wherein the arcuate hole is divided into two arcuate hole sections by a reinforcement link of said tip body.

17. The ultrasonic endoscope according to claim 11, further comprising:
first and second grooves for cooperatively fixing an inflatable balloon onto the ultrasonic endoscope, said first and second grooves being respectively formed in said tip body and said ultrasonic probe.

18. An ultrasonic endoscope comprising:
a tip body having a cylindrical outer surface, and a first groove formed in a part of the cylindrical outer surface;
an ultrasonic probe having a cylindrical inner surface, and a second groove formed in a part of the cylindrical inner surface, the cylindrical inner surface of said ultrasonic probe being fitted on the cylindrical outer surface of said tip body;
an anti-rotation member engaged with the first and second grooves when the cylindrical inner surface of said ultrasonic probe is fitted on the cylindrical outer surface of said tip body, to thereby prevent relative rotation between said ultrasonic probe and said tip body.

19. An ultrasonic endoscope according to claim 18, wherein said ultrasonic probe includes:
a receptacle having a first annular end portion defining the part of the cylindricall inner surface, a second annular end portion, and a strut connecting the first annular end portion to the second annular end portion;
a generally annular array of ultrasonic vibrators held by and between the first and second annular end portions in a longitudinal direction of said receptacle and by the strut in a circumferential direction of said receptacle; and
a flexible board extending from the generally annular array and passed between an interior of the first annular end portion of said receptacle and the cylindrical outer surface of said tip body.

20. The ultrasonic endoscope according to claim 18, further comprising:
an arcuate hole formed in said tip body within a predetermined angular range with respect to the longitudinal axis of said tip body, wherein a flexible board extending from the ultrasonic endoscope is passed through the arcuate hole; and an opening for inflating and deflating a balloon, the opening being formed in said tip body outside the predetermined angular range.

21. The ultrasonic endoscope according to claim 20, further comprising:

a water drain and injection channel formed in said tip body outside the predetermined angular range; and an air exhaust channel formed in said tip body outside the predetermined angular range;

wherein both of the channels communicate with the opening.

22. The ultrasonic endoscope according to claim 21, wherein the arcuate hole is divided into two arcuate hole sections by a reinforcement link of said tip body.

23. The ultrasonic endoscope according to claim 18, further comprising:

first and second grooves for cooperatively fixing an inflatable balloon onto the ultrasonic endoscope, said first and second grooves being respectively formed in said tip body and said ultrasonic probe.

24. An united assembly of an ultrasonic probe to be used in an ultrasonic endoscope, comprising:

a receptacle having a first annular end portion, a second annular end portion, and a strut connecting the first annular end portion to the second annular end portion;

a generally annular array of ultrasonic vibrators held by and between the first and second annular end portions in a longitudinal direction of said receptacle and by the strut in a circumferential direction of said receptacle; and a flexible board extending from the generally annular array and passed through an interior of the first annular end portion.

* * * * *